United States Patent
Miller

(10) Patent No.: US 8,227,367 B2
(45) Date of Patent: *Jul. 24, 2012

(54) REMOVAL OF WATER AND SALTS FROM A CATALYST REGENERATOR TO MAINTAIN CATALYST ACTIVITY

(75) Inventor: Lawrence W. Miller, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 1318 days.

This patent is subject to a terminal disclaimer.

(21) Appl. No.: 11/387,307

(22) Filed: Mar. 23, 2006

(65) Prior Publication Data

US 2007/0224098 A1 Sep. 27, 2007

(51) Int. Cl.
*B01J 38/12* (2006.01)
(52) U.S. Cl. ......... 502/38; 502/514; 423/240 R
(58) Field of Classification Search ......... 502/34, 502/38, 39, 514, 516; 423/240 R, 215.5
See application file for complete search history.

(56) References Cited

U.S. PATENT DOCUMENTS

| 2,892,770 A | 6/1959 | Coley et al. | |
|---|---|---|---|
| 4,310,440 A | 1/1982 | Wilson et al. | 252/435 |
| 5,558,767 A * | 9/1996 | Ressl | 208/105 |
| 6,245,703 B1 | 6/2001 | Kuechler et al. | 502/22 |
| 2004/0034264 A1 | 2/2004 | Janssen et al. | 585/639 |
| 2004/0034265 A1 | 2/2004 | Janssen et al. | 585/640 |
| 2006/0040821 A1 | 2/2006 | Pujado | 502/34 |
| 2007/0207915 A1* | 9/2007 | Pujado | 502/34 |
| 2007/0243996 A1* | 10/2007 | Pujado | 502/38 |

* cited by examiner

*Primary Examiner* — Stuart Hendrickson
*Assistant Examiner* — Richard M Rump
(74) *Attorney, Agent, or Firm* — Mark Goldberg

(57) ABSTRACT

The invention relates to a conversion process for making olefin(s) using a molecular sieve catalyst composition. More specifically, the invention is directed to a process for converting a feedstock comprising an oxygenate in the presence of a molecular sieve catalyst composition, wherein the air feed to the catalyst regenerator is free of or substantially free of metal salts. The air feed is first cooled to remove water and then washed with water to remove essentially all salts from said air feed. The water removed in the cooling step is preferably recirculated to wash the salts from the air feed.

8 Claims, No Drawings

REMOVAL OF WATER AND SALTS FROM A CATALYST REGENERATOR TO MAINTAIN CATALYST ACTIVITY

FIELD OF THE INVENTION

The present invention relates to a conversion process for making olefin(s) using a molecular sieve catalyst composition in the presence of a hydrocarbon feedstock in which the air to the catalyst regenerator is dried and then washed to remove salts to maintain catalyst activity. More particularly, the present invention involves an air blower sending heated air to a cooler in which water is removed by condensation and then the air is sent to a scrubber in which water is used to wash air borne salts from the air or other gas.

BACKGROUND OF THE INVENTION

The petrochemical industry has known for some time that oxygenates, especially alcohols, are convertible into light olefins. There are numerous technologies available for producing oxygenates including fermentation or reaction of synthesis gas derived from natural gas, petroleum liquids, carbonaceous materials including coal, recycled plastics, municipal waste or any other organic material.

The preferred methanol conversion process is generally referred to as a methanol-to-olefins (MTO) process, where methanol is converted primarily to ethylene and/or propylene in the presence of a molecular sieve which in turn can be used as the basic ingredients for polymers such as polyethylene and polypropylene. Molecular sieves have a crystalline pore structure with uniform sized pores of molecular dimensions that selectively adsorb molecules that can enter the pores, and exclude those molecules that are too large.

There are many different types of molecular sieves to convert a feedstock, especially a feedstock containing an oxygenate, into one or more olefins. For example, in U.S. Pat. No. 4,310,440 is disclosed a process of producing light olefin(s) from an alcohol using crystalline aluminophosphates, often represented by $ALPO_4$. The most useful molecular sieves for converting methanol to olefin(s) are silicoaluminophosphate molecular sieves.

These molecular sieves have been found to be sensitive to various contaminants resulting in the lowering of the yield of light olefins and even affecting the operability of a conversion process. Such contaminants are introduced to a particular conversion process in a variety of ways. Sometimes the molecular sieve itself produces contaminants affecting the conversion performance of the molecular sieve. In addition, in large scale processes, it is more likely that the effect of various contaminants entering into commercial conversion processes is higher. Contaminants can be introduced into the oxygenate feedstock or in the air that is introduced, especially into the catalyst regenerator. Unfortunately, it has been found that contaminants such as salts become concentrated over time to the extent that olefin yields are significantly impacted. In addition, the exposure of the catalyst to very high temperature steam in the regenerator has a significant contribution to the deactivation of the catalyst. We refer to this deactivation as "hydrothermal deactivation." Temperatures in the regenerator are typically about 625° C. or higher as compared to about 475° C. in a methanol-to-olefins reactor. Due to the adverse effects of these higher temperatures upon catalyst activity, in the present invention it has been found very important to keep the moisture level as low as reasonably possible within the regenerator.

Therefore, it is highly desirable to control contamination so as not to adversely affect the molecular sieve catalyst. Controlling contamination is particularly desirable in oxygenate to olefin reactions, particularly in methanol to olefin reactions, where feedstocks and catalysts are relatively expensive. It has now been found highly desirable to dry, or at least partially dry the air to the regenerator in order to significantly reduce the rate of catalyst deactivation caused by exposure to steam in the regenerator.

In addition, it has been previously reported by Janssen et al. in US 2004/0034264 A1 and US 2004/0034265 A1 that feedstocks need to be free or substantially free of salts. However, it has now been found that serious damage to the catalyst can be caused by exposure of the catalyst to the sodium chloride that is present in the air in coastal areas such as where petrochemical plants are frequently located. The present invention provides a process to protect the catalyst from harm from this and other salts that may be present in the air entering the reactor and particularly regarding air entering the catalyst regeneration vessel.

SUMMARY OF THE INVENTION

The present invention relates to a process of regenerating a molecular sieve catalyst comprising: removing moisture and airborne salts from air prior to the air being sent into a catalyst regenerator, introducing a spent molecular sieve catalyst into the regenerator; and heating the molecular sieve catalyst for a sufficient period of time and at a sufficient temperature to regenerate said molecular sieve catalyst.

This invention provides for a process for converting a feedstock in the presence of a molecular sieve into one or more olefin(s), while controlling contamination of the catalyst. Contamination of the catalyst can be lessened by providing a regeneration air feed having a reduced content of moisture and essentially no salt. The molecular sieve catalysts used in the present invention require periodic regeneration in order to maintain the catalyst activity. The catalyst regenerators need to have a stream of air entering the regenerator in order to provide the oxygen needed in burning off carbonaceous deposits on the catalyst. It has been found advantageous to condense water and salt from the air entering the regenerator. There may be a main air blower to send air to the regenerator. Due to the heat of compression, this air will be heated, usually to a temperature about 149° to 204° C. (300° to 400° F.). In the startup of the reactor, an air heater may be used so that the regenerator reaches the appropriate operating temperature. Before entering the regenerator, the air is sent to a discharge cooler in which water condenses out of the air stream. Then the air is sent into a scrubber in order to remove air borne salts. The water that has been removed in the cooler now is used to wash the salts out of the air. Supplemental water may be added, if necessary, for this purpose. While the water content of the air is somewhat increased within the scrubber if supplemental water is added, the air still remains sufficiently dry to maintain catalyst longevity. It has been found that the combination of the cooler and scrubber is a simpler, less expensive means to introduce dryer, salt free air to the catalyst regenerator than is provided in prior art such as that disclosed in U.S. Ser. No. 11/287,032 which teaches the use of a rotary adsorbent contactor or an adsorbent wheel that is positioned so that the air stream passes through an adsorbent sector of the adsorbent wheel to be dried prior to passing through the regenerator. The present invention is also simpler than taught in US 2006/0040821 A1, published Feb. 23, 2006 in which adsorbent beds are used to dry the air to a much greater extent than has been found necessary in the present invention. We have found that moderate drying of the air stream so that the air contains about 25 to 60% water as compared to ambient air together with removal of essentially all the salts contained in the air allows for maintaining a significant level of catalyst activity.

DETAILED DESCRIPTION OF THE INVENTION

The invention is directed toward a conversion process of a hydrocarbon feedstock, particularly methanol, in the presence of molecular sieve catalyst composition to one or more olefin(s). In this invention, gas fed to a catalyst regenerator is low in contaminants and particularly low in moisture and salts, so as not to significantly have an adverse effect on catalyst life or selectivity in conversion of the feed stream to produce the desired product. The gas to the catalyst regenerator has a lowered amount of water, but is only moderately drier as compared to the untreated gas (normally air).

According to this invention, some reduction in catalyst life is expected as a result of regeneration air containing contaminants, including contaminants that are present in the regeneration air due to proximity to seawater. These contaminants are more particularly water and Group IA and/or Group-IIA metal contaminants such as sea borne salts.

The catalysts used in methanol to olefins reactions is sensitive to high temperatures in the presence of moisture, which is also referred to as hydrothermal deactivation. Temperatures are higher in the regenerator (about 625° C. or more) and it is important at those temperatures to reduce the moisture level. The catalyst is also poisoned and deactivated by exchangeable metals in the feed, particularly sodium ions. Accordingly, steps need to be taken to eliminate any sodium, mostly from NaCl, that may be present in any feed streams to the reactor.

Typically, within the reactor, reaction conditions are about 475° C. at 138 kPa (20 psig) and about 60 mol-% steam in the reactor effluent, or about 1.4 bar abs. partial pressure of stream. This steam is generated as a reaction byproduct and cannot be reduced when the feed to the reactor is pure methanol. The only way to reduce the level of steam by control of the feed stream would be to feed dimethyl ether or dimethyl ether/methanol blends to the reactor.

The methanol-to-olefins catalyst regenerator typically operates at an average temperature of about 625° C. and 138 kPa (20 psig). In the regenerator there are two sources of steam, the moisture that comes into the regenerator with the air and the steam generated by combustion of the hydrogen contained in the coke being burned off the catalyst. A typical coke formula is $CH_{1.6}$ to $CH_{1.8}$. If the air is moist, for example about 3.74 mol-% water and there is up to 30% excess oxygen, the flue gas will contain about 7.57 mol-% steam corresponding to a steam partial pressure of about 0.18 bar abs. Although this partial pressure of steam is much lower than the steam pressure in the reactor, the higher temperature in the regenerator has been calculated to result in a 60% contribution to the rate of deactivation of the catalyst which under these conditions is estimated to be about 0.67% per day (0.26% from the reactor and 0.41% from the regenerator).

In the present invention it has been found that the rate of deactivation can be reduced by drying or partially drying the air going to the regenerator. When dry air is used, the flue gas will contain about 4.35 mol-% steam, corresponding to a partial pressure of about 0.10 bar abs., and resulting in an overall deactivation rate of about 0.50% per day (0.26% from the reactor and 0.24% from the regenerator). Therefore, the rate of catalyst deactivation is reduced by about 40%.

Many plants are likely to be located near a coast line where it is common to have saline aerosols present in the air. If the inlet air to the regenerator contains as low a level of salt as 1 wt-ppb sodium, it would result in the buildup of about 1.0 to 1.5 ppm sodium on the catalyst within one year of operation. It is likely that the inlet air contains significantly more sodium than one part per billion with proportionately higher buildup of sodium on the catalyst. Sodium and other exchangeable metals are known to be irreversible catalyst poisons for the conversion of oxygenates to olefins because they neutralize active acid sites on the catalyst. An increase in sodium content leads to the progressive loss of catalyst activity. Therefore it is important to provide a means to dry the air and purify the air to the regenerator in order to decrease the rate of catalyst deactivation.

Catalysts suitable for catalyzing the oxygenate-to-olefin conversion reaction of the present invention include molecular sieve catalysts. Molecular sieve catalysts can be zeolitic (zeolites) or non-zeolitic (non-zeolites). Useful catalysts may also be formed from mixtures of zeolitic and non-zeolitic molecular sieve catalysts. Desirably, the catalyst is a non-zeolitic molecular sieve.

Useful zeolitic molecular sieve catalysts include, but are not limited to, mordenite, chabazite, erionite, ZSM-5, ZSM-34, ZSM-48 and mixtures thereof. Methods of making these catalysts are known in the art and need not be discussed here.

Silicoaluminophosphates ("SAPOs") are one group of non-zeolitic molecular sieve catalysts that are useful in the present invention. Processes for making useful SAPOs are known in the art. In particular, small pore SAPOs are desired. Suitable SAPOs for use in the invention include, but are not necessarily limited to, SAPO-34, SAPO-17, SAPO-18, SAPO-44, SAPO-56 and mixtures thereof. In a more desired embodiment, the SAPO is SAPO-34.

Substituted SAPOs form a class of molecular sieves known as "MeSAPOs," which are also useful in the present invention. Processes for making MeSAPOs are known in the art. SAPOs with substituents, such as MeSAPOs, also may be suitable for use in the present invention. Suitable substituents, "Me," include, but are not necessarily limited to, nickel, cobalt, manganese, zinc, titanium, strontium, magnesium, barium, and calcium. Desired MeSAPOs are small pore MeSAPOs having pore size smaller than about 5 angstroms. Small pore MeSAPOs include, but are not necessarily limited to NiSAPO-34, CoSAPO-34, NiSAPO-17, CoSAPO-17, and mixtures thereof.

Aluminophosphates (ALPOs) with substituents, also known as "MeALPOs," are another group of molecular sieves that may be suitable for use in the present invention, with desired MeAPOs being small pore MeALPOs. Processes for making MeALPOs are known in the art. Suitable substituents include, but are not necessarily limited to nickel, cobalt, manganese, zinc, titanium, strontium, magnesium, barium, and calcium. The catalyst may be incorporated into a solid composition, preferably solid particles, in which the catalyst is present in an amount effective to promote the desired conversion reaction. The solid particles may include a catalytically effective amount of the catalyst and matrix material, preferably at least one of a filler material and a binder material, to provide a desired property or properties, e.g., desired catalyst dilution, mechanical strength and the like, to the solid composition.

The most preferred molecular sieves are silicoaluminophosphates that have eight rings and an average pore size less than about 5 angstroms, preferably in the range of from 3 to about 5 angstroms, more preferably from 3 to about 4.5 angstroms, and most preferably from 3.5 to about 4.2 angstroms.

The most preferred molecular sieves are SAPO molecular sieves, and metal substituted SAPO molecular sieves. The metal is selected from the group consisting of Co, Cr, Cu, Fe, Ga, Ge, Mg, Mn, Ni, Sn, Ti, Zn and Zr, and mixtures thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal-containing molecular sieves thereof.

The molecular sieve catalyst compositions described above are particularly useful in conversion processes of different feedstock. Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methylethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock containing oxygenates, more particularly a feedstock containing an alcohol, is converted primarily into one or more olefin(s). The olefin(s) or olefin monomer(s) produced from the feedstock typically have 2 to 4 carbons atoms, with some higher carbon byproducts, and most preferably are ethylene and/or propylene.

The process of the present invention is generally referred to as gas-to-olefins (GTO) or alternatively, methanol-to-olefins (MTO). In an MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The feedstock entering the reactor system is preferably converted, partially or fully, in the first reactor zone into a gaseous effluent that enters the disengaging vessel along with a coked molecular sieve catalyst composition. Cyclone(s) within the disengaging vessel are designed to separate the molecular sieve catalyst composition, preferably a coked molecular sieve catalyst composition, from the gaseous effluent containing one or more olefin(s) within the disengaging zone.

The disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system.

The conversion temperature employed in the conversion process, specifically within the reactor system, is in the range of from about 200° to about 1000° C., preferably from about 250° to about 800° C., most preferably from about 350° to about 550° C.

The conversion pressure employed within the reactor system varies over a wide range including autogenous pressure. The conversion pressure is based on the partial pressure of the feedstock exclusive of any diluent therein. Typically the conversion pressure employed in the process is in the range of from about 0.1 kPa to about 5 MPa, preferably from about 5 kPa to about 1 MPa, and most preferably from about 20 kPa to about 500 kPa.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. In most designs, the regeneration medium is air. The regeneration conditions are those capable of burning coke from the coked catalyst composition, preferably to a level less than about 0.5 wt-% based on the total weight of the coked molecular sieve catalyst composition entering the regeneration system. The molecular sieve catalyst composition withdrawn from the regenerator forms a regenerated molecular sieve catalyst composition. Air being fed to a catalyst regenerator can be dried in order to reduce the level of hydrothermal damage on the catalyst due to the combination of moisture and high temperatures. For example, if the inlet air is humid with about 4.0 mol-% moisture content, the outlet gas from a regenerator will contain about 7.5 mol-% moisture. At 625° C., exposure of the catalyst to this hot and humid gas may result in a relative activity loss of about 0.4 to 0.6% per day. However, if the inlet air is dried, the offgas from the regenerator will only contain about 3.5 mol-% moisture. At 625° C., exposure of the catalyst to these conditions will result in a relative activity loss of about 0.1 to 0.3% per day.

In accordance with the present invention, the air stream entering the regenerator has some water removed. When the air stream is relatively dry, little or no water will be removed, however. Applicants have also found that the air entering the regeneration vessel can be a significant source of undesired salt. For example, if the air salinity contains 0.5 ppm sodium, over time without catalyst withdrawals or additions, the level of sodium on the catalyst could reach about 4500 wt-ppm, which would result in a significant loss of active sites. Preferably, the air salinity is from 0 to 100 wt-ppb. If, for example, the air salinity can be reduced to 30 wt-ppb, the buildup of sodium on the catalyst under similar conditions would be only 20 to about 250 wt-ppm, which has no significant effect on the activity of the catalyst. More preferably, the air salinity is from 0 to 50 wt-ppb and even more preferably the air salinity is in a range from 0-20 wt-ppb or below measurable limits. For long-term catalyst stability, it is desirable to maintain the sodium level below 500 wt-ppm. A condenser is used to first separate water and some sodium as well as other impurities. The water would be retained to be circulated over the air on several trays or other contacting means such as packing or other materials that cause contact between the water and air to wash out the salts. If necessary in the event the air is low in relative humidity, additional water from outside the system can be first added to the air to wash out at least a portion of the sodium content followed by drying to remove added water as well as residual water. In earlier reactor designs, atmospheric air would have been heated and sent to a catalyst regenerator. An air blower would be used to send heated air at about 121° to 204° C. (250° to 400° F.) into the catalyst regenerator. In the case of FCC units, the value of the catalyst is low enough that supplemental methods are not necessary to extend the life span of the catalyst. However, in connection with a more valuable catalyst system, such as the SAPO-34 catalyst used with the methanol to olefins process, it is economically advantageous to remove airborne salts as well as humidity from the regeneration air.

In order to deal with this problem, a cooler is added to the air discharged from the air blower and a scrubber is added to wash the salts from the air. It has now been found that if the heated atmospheric air from the air blower is cooled to for example, about 38° C. (100° F.), a portion of the water in the air flow condenses (unless the air is low humidity air). In the present invention, it has been found that this condensed water can be recirculated to a scrubber to scrub or wash out much of the air borne salt with the atmospheric air flow. The water that has been removed from the air is circulated over the air using a pump and several contact trays or other contacting means can be included within the scrubber to increase contact time between the air and water. The water will thereby remove the salt from the air. As the water level rises within the scrubber, it is removed from the scrubber. The removed water will have a very small concentration of salts so that the water will not require special treatment. The use of the water within the scrubber will result in an incidental increase in humidity. If further drying is desired, supplemental driers can be added to the system.

EXAMPLE

In a tropical location, atmospheric air is at 32° C. (90° F.) and 75% relative humidity. If the discharge from the blower is at 35 psig and the conditions within the scrubber are 38° C. (100° F.) at 30 psig, approximately 42% of the water and essentially all of the salts will be removed from the scrubber.

The catalyst regeneration temperature in the regenerator is in the range of from about 2000 to about 1500° C., preferably from about 3000 to about 1000° C., more preferably from about 450° to about 750° C., and most preferably from about 550° to 700° C. The regeneration pressure is in the range of from about 103 to about 3448 kPa, preferably from about 138 to about 1724 kPa (20 to 250 psia), more preferably from about 172 to about 1034 kPa (25 to 150 psia), and most preferably from about 207 to about 414 kPa (30 to 60 psia). The preferred residence time of the molecular sieve catalyst composition in the regenerator is in the range of from about one minute to several hours, most preferably about one minute to 100 minutes, and the preferred volume of oxygen in the gas exiting the regenerator is in the range of from about 0.01 to about 5 mol-% based on the total volume of the gas. The gas exiting the regenerator will contain CO and $CO_2$ that result from the combustion of carbonaceous materials. Because of the presence of residual oxygen in the offgas, post-combustion of CO may take place in the gaseous phase.

What is claimed is:

1. A process of drying and purifying air flowing to a catalyst regeneration vessel comprising:
    a) introducing a warm regeneration gas comprising air;
    b) then cooling said regeneration gas to a temperature at which a substantial portion of water content is condensed and removed from said regeneration gas;
    c) then sending said regeneration gas to a scrubber;
    d) then passing a quantity of water through said scrubber to remove salts from said regeneration gas; and
    e) sending said regeneration gas to said catalyst regeneration vessel to regenerate a SAPO-34 catalyst.

2. The process of claim 1 wherein said water removed in step b) is at least a portion of said quantity of water in step d).

3. The process of claim 1 wherein said scrubber contains contacting means to contact said regeneration gas with said water.

4. The process of claim 3 wherein said contacting means comprise at least two contact trays.

5. The process of claim 1 wherein said salt is selected from the group consisting of sodium chloride, lithium chloride and potassium chloride.

6. The process of claim 1 wherein said regeneration gas contains less water upon entering said catalyst regeneration vessel as compared to prior to the cooling of said regeneration gas.

7. The process of claim 1 wherein said regeneration gas contains about 0 to 50 ppb sodium from NaCl prior to being cooled.

8. The process of claim 1 wherein a SAPO-34 catalyst for conversion of oxygenates to olefins is regenerated in said catalyst regeneration vessel.

* * * * *